United States Patent
Folluo et al.

(10) Patent No.: US 11,980,531 B2
(45) Date of Patent: May 14, 2024

(54) PROTECTIVE RING FOR TAMPON APPLICATOR

(71) Applicants: Sarah Folluo, Salt Lake City, UT (US); Ian Hammond, Salt Lake City, UT (US)

(72) Inventors: Sarah Folluo, Salt Lake City, UT (US); Ian Hammond, Salt Lake City, UT (US)

(*) Notice: Subject to any disclaimer, the term of this patent is extended or adjusted under 35 U.S.C. 154(b) by 64 days.

(21) Appl. No.: 17/697,883

(22) Filed: Mar. 17, 2022

(65) Prior Publication Data

US 2022/0296433 A1    Sep. 22, 2022

Related U.S. Application Data

(60) Provisional application No. 63/231,834, filed on Aug. 11, 2021, provisional application No. 63/162,361, filed on Mar. 17, 2021.

(51) Int. Cl.
*A61F 13/26* (2006.01)
*A61F 13/20* (2006.01)

(52) U.S. Cl.
CPC ........ *A61F 13/266* (2013.01); *A61F 13/2071* (2013.01)

(58) Field of Classification Search
CPC ...... A61F 13/26; A61F 13/263; A61F 13/266; A61F 13/268; A61F 13/2071
See application file for complete search history.

(56) References Cited

U.S. PATENT DOCUMENTS

| | | | |
|---|---|---|---|
| 3,042,040 A | 7/1962 | Galik | |
| 3,667,465 A * | 6/1972 | Voss | A61M 31/007 604/218 |
| 4,198,978 A | 4/1980 | Nigro | |
| 5,397,332 A * | 3/1995 | Kammerer | A61B 17/0057 606/198 |
| 6,190,348 B1 | 2/2001 | Tiemann et al. | |
| 2008/0167599 A1 | 7/2008 | Osborn et al. | |
| 2011/0270150 A1 | 11/2011 | Karapasha et al. | |
| 2013/0331763 A1 | 12/2013 | Ito et al. | |
| 2014/0046239 A1 * | 2/2014 | Taniguchi | A61F 13/266 604/11 |
| 2014/0052048 A1 | 2/2014 | Taniguchi et al. | |
| 2016/0008118 A1 | 1/2016 | Bravo | |
| 2018/0104113 A1 * | 4/2018 | Buell | A61F 13/5511 |

FOREIGN PATENT DOCUMENTS

| | | | | |
|---|---|---|---|---|
| JP | 2008178531 A * | 8/2008 | | A61F 13/202 |
| WO | WO-2013080756 A1 * | 6/2013 | | A61F 13/26 |

OTHER PUBLICATIONS

MATOS "PCT International Search Report for International Application No. PCT/US2022/020832" dated Jun. 21, 2022, 2 pages.
MATOS "Written Opinion of the International Searching Authority for International Application No. PCT/US2022/020832" dated Jun. 21, 2022, 7 pages.

* cited by examiner

*Primary Examiner* — Susan S Su
(74) *Attorney, Agent, or Firm* — Intellectual Strategies (57) ABSTRACT

A tampon applicator system includes a body and a protective ring extending outward from the body. The body includes a pinch zone and an opening. The pinch zone is disposed on the body below the protective ring and on an opposite side of the body from the opening. The protective ring is configured to protect the pinch zone from exposure on the opposite side of the protective ring.

15 Claims, 5 Drawing Sheets

PROTECTIVE RING FOR TAMPON APPLICATOR

RELATED APPLICATIONS

This application claims the benefit of U.S. Provisional Patent Application No. 63/231,834, filed Aug. 11, 2021, which is incorporated herein by reference in its entirety. This application also claims the benefit of U.S. Provisional Patent Application No. 63/162,361, filed Mar. 17, 2021, which is incorporated herein by reference in its entirety.

BACKGROUND

This disclosure relates generally to an environmentally friendly and/or sustainable tampon applicator.

SUMMARY

The subject matter of the present application has been developed in response to the present state of the art, and in particular, in response to the problems and disadvantages associated with conventional tampon applicators that have not yet been fully solved by currently available techniques. Accordingly, the subject matter of the present application has been developed to provide embodiments of a system, apparatus, and method that overcome at least some of the shortcomings of prior art techniques.

Disclosed herein is a tampon applicator system. The tampon applicator system includes a body and a protective ring extending outward from the body. The body includes a pinch zone and an opening. The pinch zone is disposed on the body below the protective ring and on an opposite side of the body from the opening. The protective ring is configured to protect the pinch zone from exposure on the opposite side of the protective ring. The preceding subject matter of this paragraph characterizes example 1 of the present disclosure.

The tampon applicator system further includes a stem. The stem is configured to slide into the body. The preceding subject matter of this paragraph characterizes example 2 of the present disclosure, wherein example 2 also includes the subject matter according to example 1, above.

The stem further comprises proximal locking beads at a proximal end of the stem and distal locking beads at a distal end of the stem. The preceding subject matter of this paragraph characterizes example 3 of the present disclosure, wherein example 3 also includes the subject matter according to any one of examples 1-2, above.

The stem is configured to slide completely within the body. The preceding subject matter of this paragraph characterizes example 4 of the present disclosure, wherein example 4 also includes the subject matter according to any one of examples 1-3, above.

The proximal locking beads are molded into the proximal end of the stem and the distal locking beads are molded into the distal end of the stem. The preceding subject matter of this paragraph characterizes example 5 of the present disclosure, wherein example 5 also includes the subject matter according to any one of examples 1-4, above.

The protective ring is molded into the body, such that the body and protective ring form a unitary piece. The preceding subject matter of this paragraph characterizes example 6 of the present disclosure, wherein example 6 also includes the subject matter according to any one of examples 1-5, above.

The protective ring is a separate piece from the body and the protective ring is mounted to the body. The preceding subject matter of this paragraph characterizes example 7 of the present disclosure, wherein example 7 also includes the subject matter according to any one of examples 1-6, above.

The body further comprises a retention structure on an exterior surface of the body. The preceding subject matter of this paragraph characterizes example 8 of the present disclosure, wherein example 8 also includes the subject matter according to any one of examples 1-7, above.

The retention structure comprises an upper protrusion and a lower protrusion. The preceding subject matter of this paragraph characterizes example 9 of the present disclosure, wherein example 9 also includes the subject matter according to any one of examples 1-8, above.

The protective ring is configured to couple to the body and be seated between the upper protrusion and the lower protrusion. The preceding subject matter of this paragraph characterizes example 10 of the present disclosure, wherein example 10 also includes the subject matter according to any one of examples 1-9, above.

The upper protrusion and the lower protrusion are angled protrusions. The preceding subject matter of this paragraph characterizes example 11 of the present disclosure, wherein example 11 also includes the subject matter according to any one of examples 1-10, above.

The retention structure comprises a depressed channel circumferentially around the body. The preceding subject matter of this paragraph characterizes example 12 of the present disclosure, wherein example 12 also includes the subject matter according to any one of examples 1-11, above.

The protective ring is configured to couple to the body and be seated in the depressed channel. The preceding subject matter of this paragraph characterizes example 13 of the present disclosure, wherein example 13 also includes the subject matter according to any one of examples 1-12, above.

The protective ring further comprises a series of slits on an inner diameter of the protective ring, the slits extending radially outward, wherein the series of slits are configured to facilitate flexing of the inner diameter while mounting the protective ring to the body. The preceding subject matter of this paragraph characterizes example 14 of the present disclosure, wherein example 14 also includes the subject matter according to any one of examples 1-13, above.

The protective ring is sloped downward towards the pinch zone and away from the opening. The preceding subject matter of this paragraph characterizes example 15 of the present disclosure, wherein example 15 also includes the subject matter according to any one of examples 1-14, above.

The body further comprises an internal structure within an interior of the body, wherein the internal structure protrudes out of an interior surface of the body and wherein the internal structure is configured to interact with a stem and locking beads on the stem. The preceding subject matter of this paragraph characterizes example 16 of the present disclosure, wherein example 16 also includes the subject matter according to any one of examples 1-15, above.

Disclosed herein is a tampon applicator system. The tampon applicator system includes a body and a protective ring detachable from the body and configured to extend outward from the body. The body includes a pinch zone, an opening, and a retention structure on an exterior surface of the body. The pinch zone is disposed on the body below the protective ring and on an opposite side of the body from the opening. The protective ring is configured to protect the pinch zone from exposure on the opposite side of the protective ring. The preceding subject matter of this paragraph characterizes example 17 of the present disclosure.

The retention structure comprises an upper protrusion and a lower protrusion. The preceding subject matter of this paragraph characterizes example 18 of the present disclosure, wherein example 18 also includes the subject matter according to example 17, above.

The protective ring is configured to couple to the body and be seated between the upper protrusion and the lower protrusion. The preceding subject matter of this paragraph characterizes example 19 of the present disclosure, wherein example 19 also includes the subject matter according to any one of examples 17-18, above.

The upper protrusion and the lower protrusion are rounded protrusions. The preceding subject matter of this paragraph characterizes example 20 of the present disclosure, wherein example 20 also includes the subject matter according to any one of examples 17-19, above.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered limiting of its scope, the subject matter will be described and explained with additional specificity and detail through the use of the drawings, in which.

Throughout the description, similar reference numbers may be used to identify similar elements. The following list is an example of the reference numbers used in the accompanying drawings.

| Reference # | Designation |
| --- | --- |
| 100 | Applicator |
| 102 | Body |
| 104 | Stem |
| 106 | Opening |
| 108 | Flap |
| 110 | Pinch Zone |
| 112 | Guard Ring or Flange |
| 114 | Distal end (of the stem) |
| 116 | Distal locking beads |
| 118 | Proximal locking beads |
| 120 | View of applicator in retracted position |
| 130 | Top view of applicator |
| 140 | Sectional view of applicator in extended position |
| 142 | Proximal end (of the stem) |
| 160 | Detailed view of proximal end locking mechanism |
| 162 | Internal structure |
| 170 | Sectional view of applicator in partially retracted position |
| 180 | Sectional view of applicator in fully retracted position |
| 190 | Detailed view of distal end locking mechanism |
| 200 | Applicator System |
| 202 | Protective Ring (first embodiment) |
| 203 | Inner Diameter |
| 204 | Protective Ring (second embodiment) |
| 205 | Slit |
| 206 | Protective Ring (third embodiment) |
| 208 | Protective Ring (fourth embodiment) |
| 210 | Detailed view of ring retainer (first embodiment) |
| 212 | Ring retainer (first embodiment) |
| 213 | Upper Protrusion |
| 215 | Lower Protrusion |
| 220 | Detailed view of ring retainer (second embodiment) |
| 222 | Ring retainer (second embodiment) |
| 223 | Upper Angled Protrusion |
| 225 | Lower Angled Protrusion |
| 230 | Detailed view of ring retainer (third embodiment) |
| 232 | Ring retainer (third embodiment) |
| 233 | Depressed Channel |

Throughout this application, similar designations or vocabulary may be used to identify similar elements, although the breadth of this disclosure should be understood to incorporate any alternatives and variations referenced within the specification (including the claims) and the accompanying drawings.

DETAILED DESCRIPTION

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments disclose a tampon applicator. In some embodiments, the tampon applicator is environmentally friendly and/or sustainable. At least some embodiments of the tampon applicator include a guard ring to maintain sanitation and hygiene, and a locking mechanism to secure the tampon applicator in a retracted position for disposal. At least some embodiments of the tampon applicator are constructed from a biodegradable and/or compostable plastic. At least some embodiments of the tampon applicator are constructed from bioplastics. At least some embodiments of the tampon applicator are constructed from MATER-BI™.

In some embodiments, the tampon applicator includes a body, a stem, proximal and distal locking beads, and a guard ring or flange. The body includes an opening, a flap, and a pinch zone. The stem has a distal end containing the distal locking beads, and a proximal end containing the proximal locking beads. In operation, a pair of noticeable snaps can be heard by a user during insertion of a tampon. A first snap will be heard when the proximal locking beads are forced into the body of the tampon applicator. A second snap will be heard when the distal locking beads are forced into the body of the tampon applicator, indicating that the tampon is fully inserted.

Figure 1:
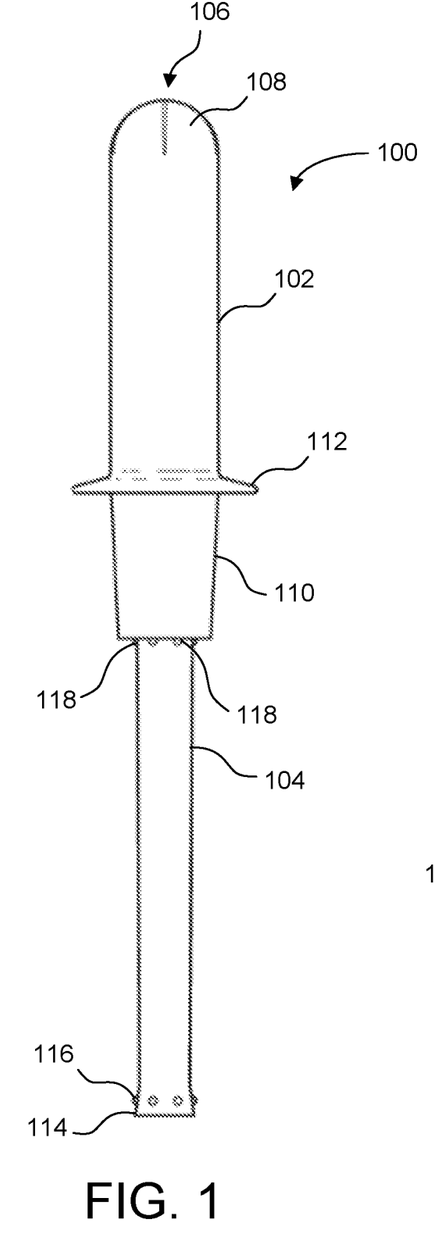
FIG. 1 depicts a tampon applicator in an extended position according to one or more embodiments of the present disclosure.

FIG. 1 depicts a tampon applicator 100 in an extended position. Although the tampon applicator 100 is shown and described with certain components and functionality, other embodiments of the tampon applicator 100 may include fewer or more components to implement less or more functionality.

The illustrated tampon applicator 100 includes a body 102 and a stem 104. The illustrated body 102 includes a guard ring 112, a pinch zone 110, and an opening 106. The opening 106 includes flap(s) 108.

In some embodiments, the guard ring 112 acts as a two-way protective shield for a user. In other parts of this specification, the guard ring 112 may be referred to as a protective ring. The guard ring 112 or protective ring extends circumferentially outward from the body 102. The guard ring 112 protects the user's fingers against germs and bacteria. Similarly, the guard ring 112 protects against the transfer of germs and bacteria present on the user's hand and fingers into the user's body.

In some embodiments, the pinch zone 110 is a grip point for the tampon applicator 100. As shown in FIG. 1, the guard ring 112 is located along a longitudinal surface of the body 102. In some embodiments, the guard ring 112 is located just above the pinch zone 110. In some embodiments, the guard ring 112 is located closer to the opening 106 than the pinch zone 110.

FIG. 1 illustrates a profile of the tampon applicator 100. As illustrated in FIG. 1, the body 102 sweeps downward toward the pinch zone 110. In some embodiments, the pinch zone 110 has a narrower circumference than a circumference of the body 102. In some embodiments, the circumference of the pinch zone is the same as the circumference of the body 102. In some embodiments, the circumference of the pinch zone 110 is larger than the circumference of the body 102.

In some embodiments, the body 102 sweeps upward toward the opening 106. In some embodiments, the profile of the tampon applicator 100 is oblong. In some embodiments, the profile of the tampon applicator 100 is cylindrical. In some embodiments, the profile of the tampon applicator 100 is substantially oval shaped.

Figure 4:
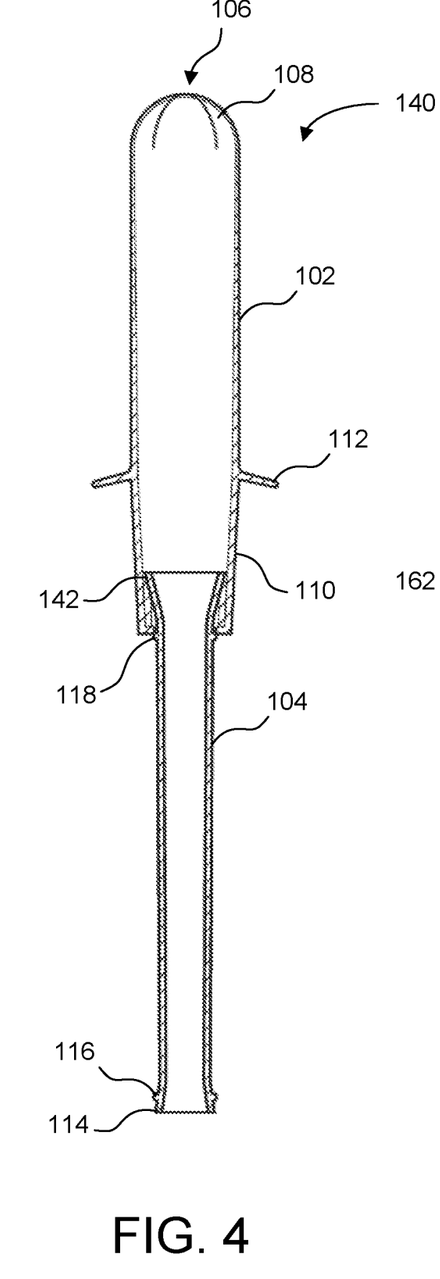
FIG. 4 depicts a sectional view of the applicator of FIG. 1 with the stem in an extended position according to one or more embodiments of the present disclosure.

The stem 104 includes a distal end 114, distal locking beads 116, proximal locking beads 118 and a proximal end 142 (refer to FIG. 4). In some embodiments, the stem 104 includes vertical ribbing and/or structural support. In some embodiments, the distal and proximal locking beads 116, 118 are molded into the distal and proximal ends 114, 142 as beads (as illustrated in FIG. 1). In some embodiments, the distal and proximal locking beads 116, 118 are elongated and oval shaped. In some embodiments, the distal and proximal locking beads 116, 118 are rectangular. In some embodiments, the distal and proximal locking beads 116, 118 are elongated such that they merge into each other to form a locking ring. Although the stem 104 is shown and described with certain components and functionality, other embodiments of the stem 104 may include fewer or more components to implement less or more functionality.

The stem 104 slides into the body 102. Initially, the proximal locking beads 118 are "locked out" of the body 102 by internal structure 162 (refer to FIG. 5). Applying slight pressure to stem 104 will force the proximal locking beads 118 past the internal structure 162 and the stem 104 will be partially contained in the body 102. In embodiments where the proximal locking beads 118 are elongated or a locking ring, application of pressure to the stem 104 will similarly force the elongated beads or ring past the internal structure 162.

When the stem 104 is fully contained inside the body 102, distal locking beads 116 will abut the internal structure 162, whether the distal locking beads 116 are beads (as illustrated in FIG. 1) or elongated or a locking ring. Applying slight pressure to stem 104 will force the distal locking beads 116 past the internal structure 162 and the stem 104 will be fully contained inside the body 102 and the applicator 100 will be ready for disposal. Distal locking beads 116 ensure the tampon applicator 100 remains in a retracted position for a more sanitary and hygienic disposal.

Figure 2:
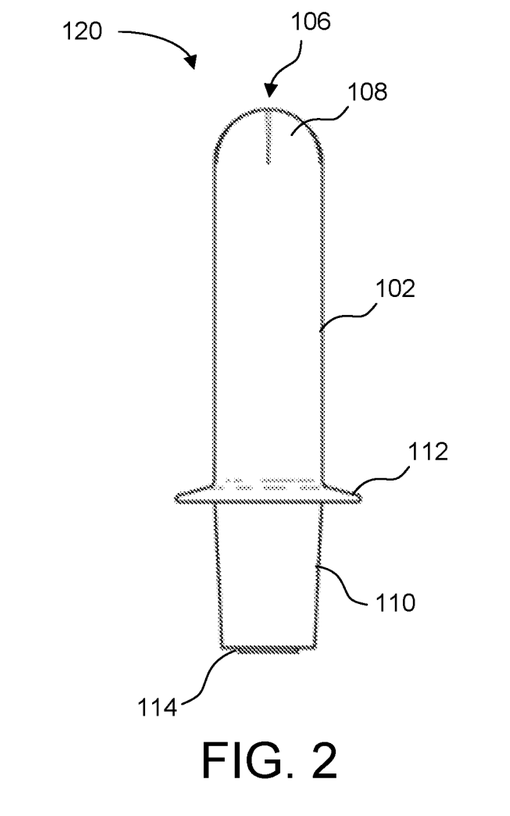
FIG. 2 depicts the applicator of FIG. 1 in a retracted position according to one or more embodiments of the present disclosure.

FIG. 2 illustrates a retracted view 120 of the tampon applicator 100. As shown in FIG. 2, distal end 114 of stem 104 (not visible in FIG. 2) abuts the pinch zone 110. In the retracted position, stem 104 is contained inside the body 102 of the tampon applicator 100. In some embodiments, the stem 104 is completely contained inside the body 102. In some embodiments, the stem 104 is substantially contained inside the body 102 with only a small portion of the distal end 114 visible. The distal locking beads 116 are contained inside the body 104.

Figure 3:
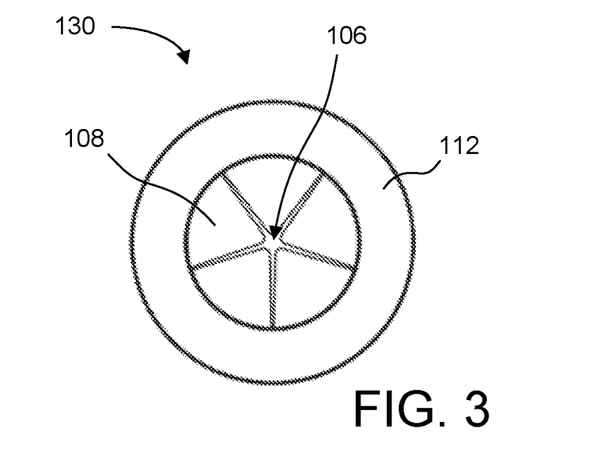
FIG. 3 depicts a top view of the applicator of FIG. 1 according to one or more embodiments of the present disclosure.

FIG. 3 illustrates a top view 130 of the tampon applicator 100. As can be seen in FIG. 3, the embodiment illustrates a top view of the flaps 108, the opening 106 and the guard ring 112.

In the embodiment depicted in FIG. 3, the opening 106 is constructed from five flaps 108, though other embodiments may have more than five or less than five flaps. For example, in some embodiments the opening 106 is constructed from three flaps, four flaps, six flaps or seven flaps. In some embodiments, the flaps 108 include perforations. In some embodiments, the flaps 108 includes scoring. In some embodiments, the flaps 108 include indented lines. In some embodiments, the flaps 108 include these or other structural features to increase the flexibility of the flaps 108.

The guard ring 112 is a protective barrier for the user's fingers to maintain sanitation and hygiene, and guard against micro-organisms. The guard ring 112 acts as a two-way protective shield for a user. The guard ring 112 protects the user's fingers against germs and bacteria. Similarly, the guard ring 112 protects against the transfer of germs and bacteria present on the user's hand and fingers into the user's body.

In some embodiments, guard ring 112 is substantially circular, giving the top view 130 a substantially circular shape. Other shapes are contemplated herein. In some embodiments, guard ring 112 is an oval shape. In some embodiments, guard ring 112 is substantially rectangular.

In some embodiments, a bottom surface of the guard ring 112 is worked to provide a grip for the user. In some embodiments, the guard ring 112 is sloped downward and the bottom surface has a convex shape. In some embodiments, the guard ring 112 may have more complex surfaces that enhance the two-way protection for the user and provide a better grip for the user.

As shown in FIG. 3, in some embodiments, the guard ring 112 has a diameter that is larger than a diameter of the body 102 (and thus the opening 106). In some embodiments, the diameter of the body 102 is fourteen millimeters and the diameter of the guard ring 112 is twenty-four millimeters. While a specific embodiment, these numbers are illustrative of the absolute size of these features but also serve as illustrative of a relative size of these features. In some embodiments, the diameter of the body 102 is sixteen millimeters and the diameter of the guard ring 112 is twenty-six millimeters. In some embodiments, the diameters of the body 102 and guard ring 112 vary by 10-20% above or below the listed values.

FIG. 4 is a sectional view 140 of the tampon applicator 100 of FIG. 1 in an extended, or "locked out," position. As shown in FIG. 4, the body 102 receives the stem 104. The proximal end 142 of the stem 104 contains the proximal locking beads 118. In some embodiments, the proximal locking beads 118 are molded into the proximal end 142 as beads. In some embodiments, the proximal locking beads 118 are elongated and oval shaped. In some embodiments, the proximal locking beads 118 are rectangular. In some embodiments, the proximal locking beads 118 are elongated such that they merge into each other to form a locking ring. In the embodiment illustrated in FIG. 4, the proximal end 142 of stem 104 is contained inside the end of the pinch zone 110 and the proximal locking beads 118 are flush with an end of the pinch zone 110.

FIG. 4 also illustrates a profile of the tampon applicator 100. As illustrated in FIG. 4, the body 102 sweeps downward toward the pinch zone 110. In some embodiments, the pinch zone 110 has a narrower circumference than a circumference of the body 102. In some embodiments, the circumference of the pinch zone is the same as the circumference of the body 102. In some embodiments, the circumference of the pinch zone is larger than the circumference of the body 102. In some embodiments, the body 102 sweeps upward toward the opening 106. In some embodiments, the profile of the tampon applicator 100 is oblong. In some embodiments, the profile of the tampon applicator 100 is cylindrical. In some embodiments, the profile of the tampon applicator 100 is substantially oval shaped.

Figure 5:
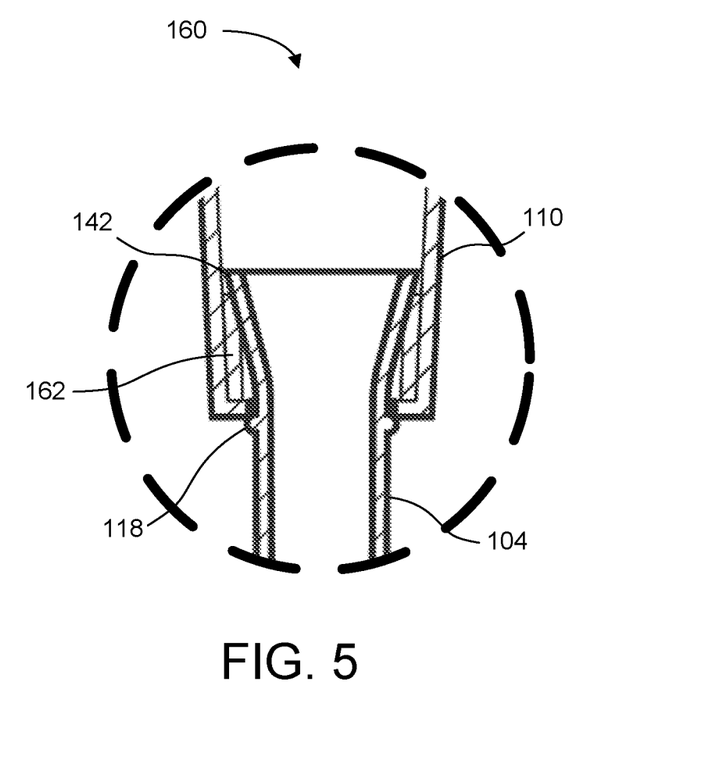
FIG. 5 depicts a detailed view of the extended locking mechanism of the applicator of FIG. 4 according to one or more embodiments of the present disclosure.

FIG. 5 depicts a detailed view of the extended locking mechanism of the applicator of FIG. 4. FIG. 5 depicts the proximal end 142, the proximal locking beads 118, the internal structure 162, the pinch zone 110 and the stem 104. The internal structure 162 is located just inside the end of the pinch zone 110. In some embodiments, the internal structure 162 includes a ring to secure the proximal locking beads 118 in place and keep the tampon applicator in the extended position. As shown in FIG. 5, when the stem 104 is in an extended (or "locked out") position, the proximal end 142 is partially contained inside the pinch zone 110 and the proximal locking beads 118 are flush with the internal structure 162. When force is applied by a user to the stem 104, the proximal locking beads 118 are forced past the internal structure 162. A noticeable snap can be heard by the user when the proximal locking beads 118 are forced past the internal structure 162.

Figure 6:
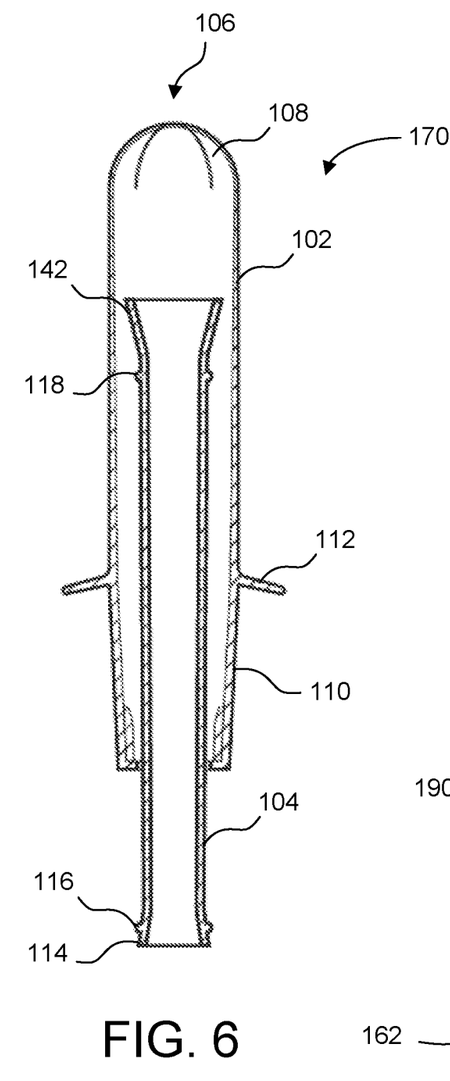
FIG. 6 depicts a sectional view of the applicator of FIG. 1 with the stem in a partially retracted position according to one or more embodiments of the present disclosure.

FIG. 6 depicts a sectional view of the applicator 100 from FIG. 1 in a partially retracted position 170. As illustrated in FIG. 6, the stem 104 is partially contained inside the body 102. The proximal end 142 and proximal locking beads 118 have been forced past the internal structure 162 and are located past the guard ring 112 inside the body 102. The distal end 114 and distal locking beads 116 extend past the pinch zone 110 and are not in contact with the internal structure 162.

Figure 7:
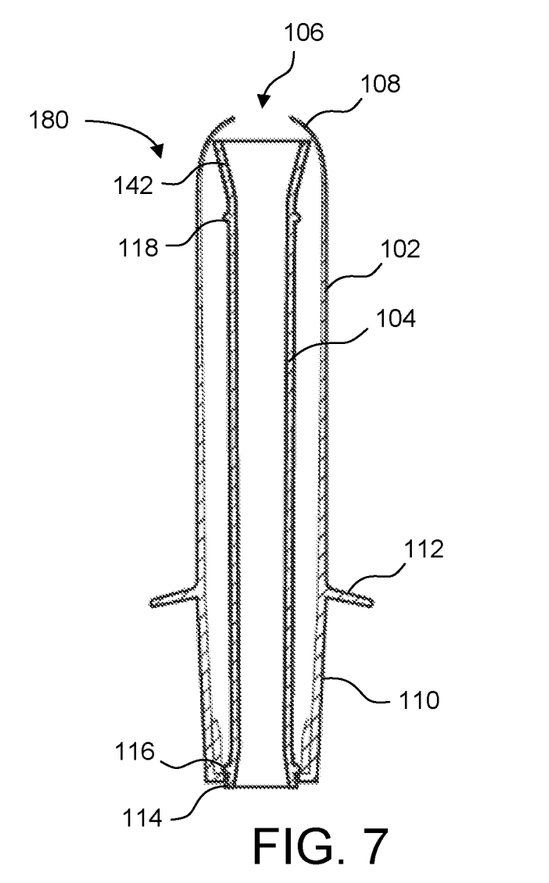
FIG. 7 depicts a sectional view of the applicator of FIG. 1 with the stem in a retracted position according to one or more embodiments of the present disclosure.

FIG. 7 depicts a sectional view of the applicator of FIG. 1 with the stem in a retracted position 180. The stem 104 is substantially, or fully, contained inside the body 102 and is "locked in." As pressure is applied by the user to the stem 104, the stem 104 is received by the body 102 and pressure is applied to the flaps 108 at an interior surface, expanding the opening 106. In some embodiments, the pressure is applied by a preloaded tampon and expansion of the opening 106 allows for insertion, and exit, of a tampon from the tampon applicator 100. In embodiments where the flaps 108 contain perforations, the flaps 108 will be more flexible in the expansion of the opening 106. In some embodiments, the flaps 108 include scoring, indented lines, or other structural features to increase the flexibility of the flaps 108.

In FIG. 7, the distal locking beads 116 are in contact with the internal structure 162 and the distal end 114 is in contact with an end of the pinch zone 110. In some embodiments, the internal structure 162 includes a ring to secure the distal locking beads in place and keep the tampon applicator in the "locked in" position. A noticeable snap can be heard by the user when the distal locking beads 116 come into contact with the internal structure 162, indicating the tampon has been fully inserted.

Figure 8:
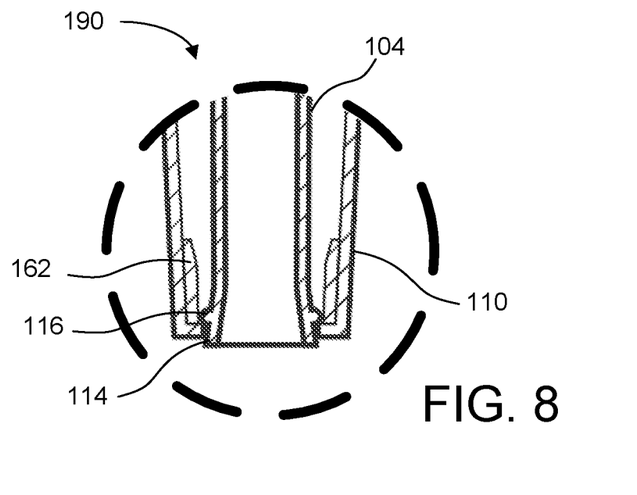
FIG. 8 depicts a detailed view of the retracted locking mechanism of the applicator of FIG. 7 according to one or more embodiments of the present disclosure.

FIG. 8 depicts a detailed view 190 of the retracted locking mechanism of the applicator of FIG. 7. As shown in FIG. 8, the distal end 114 is flush with the end of the pinch zone 110 and the distal locking beads 116 are in contact with the internal structure 162. The stem 104 is "locked in" to the body 102 and secured for a more sanitary and hygienic disposal. In some embodiments, the distal locking beads 116 are molded into the distal end 114 as beads. In some embodiments, the distal locking beads 116 are elongated and oval shaped. In some embodiments, the distal locking beads 116 are rectangular. In some embodiments, the distal locking beads 116 are elongated such that they merge into each other to form a locking ring.

In some embodiments, the applicator 100 is constructed from biodegradable materials, such as bioplastic or compostable plastic. In some embodiments, the applicator 100 is constructed from MATER-BI™ plastic. In some embodiments, the applicator 100 is constructed from a substantially vegetable oil-based material. Applicator 100 can be constructed from any other environmentally friendly and sustainable material.

Figures 9, 10, 11, 12, 13:
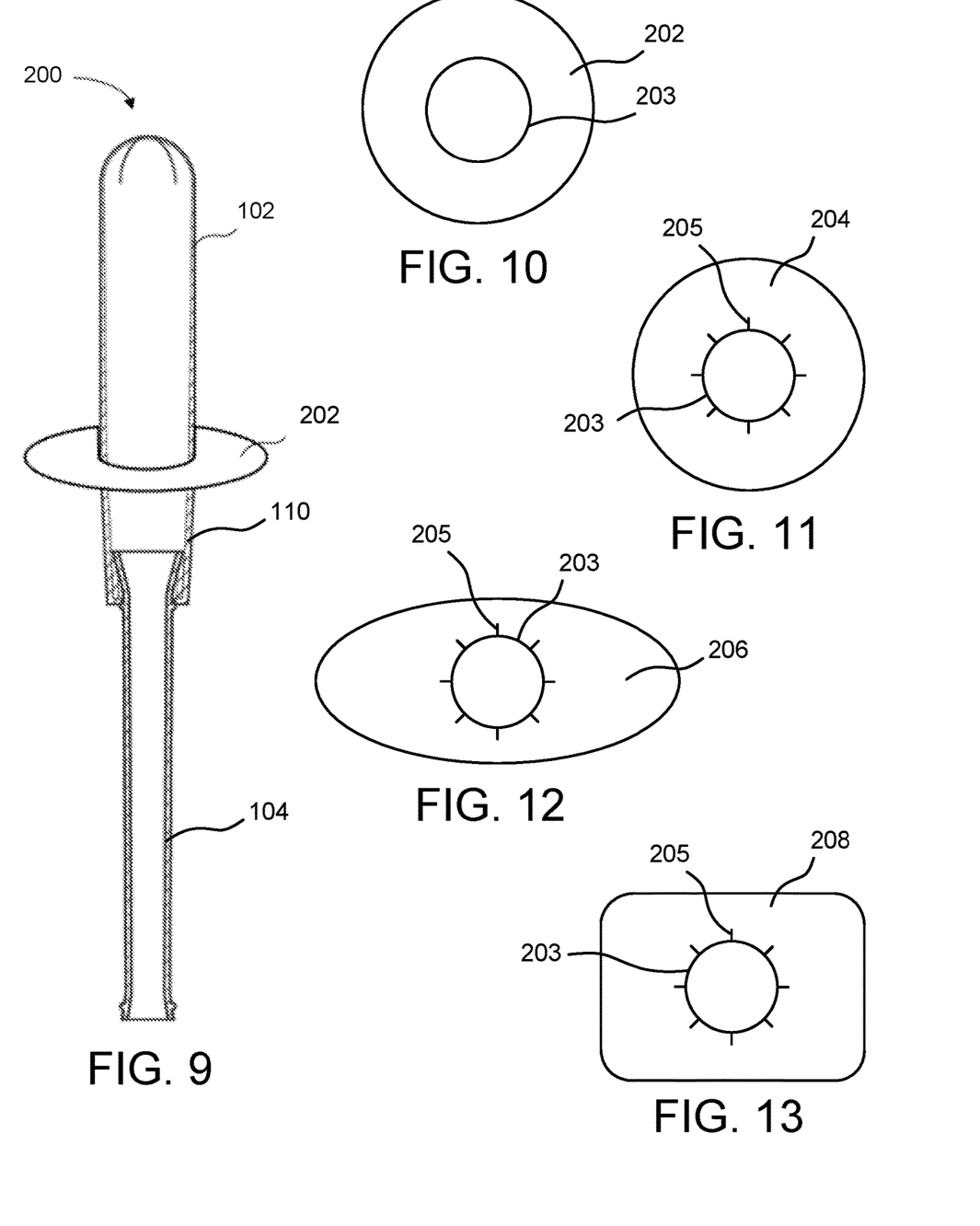
FIG. 9 depicts one embodiment of a tampon applicator system according to one or more embodiments of the present disclosure.
FIG. 10 depicts a top view of the protective ring of FIG. 9 according to one or more embodiments of the present disclosure.
FIG. 11 depicts a top view of another embodiment of a protective ring according to one or more embodiments of the present disclosure.
FIG. 12 depicts a top view of another embodiment of a protective ring according to one or more embodiments of the present disclosure.
FIG. 13 depicts a top view of another embodiment of a protective ring according to one or more embodiments of the present disclosure.

FIG. 9 depicts one embodiment of a tampon applicator system 200. The illustrated applicator system 200 includes an applicator body 102 and a protective ring 202. In some embodiments, the protective ring 202 is attachable to and detachable from the body 102 of the applicator.

In the illustrated embodiment, the body 102 and stem 104 are shown in a cutaway view while the protective ring 202 is shown fully (not cutaway) to illustrate the positioning of the protective ring 202 on the body 102.

FIG. 10 depicts a top view of the protective ring 202 of FIG. 9. In the illustrated embodiment, the protective ring 202 is a ring of thin material that has sufficient durability to be attached to the body 102 of the applicator and maintain its rigidity to extend outward from the body 102. This allows a user to handle the applicator while providing a protective material or shield from fluids.

The protective ring 202 may come in a variety of shapes and sizes. In some embodiments, the inner diameter 203 of the protective ring 202 is the same size or slightly smaller than the outer diameter of the body 102. In other embodiments, the inner diameter 203 of the protective ring 202 may be slightly larger than the outer diameter of the body 102, especially in embodiments where additional retainers help to hold the protective ring 202 in place along the length of the body 102. Additionally, the protective ring 202 can be thin, thick, or in some cases have a variable thickness to provide a desired level of flexibility, rigidity, or other physical handling characteristics.

Also, embodiments of the protective ring 202 may be able to stretch or maintain rigidity. Embodiments that exhibit some elasticity may be suitable for use in any of the mounting application described herein. In some embodiments, the protective ring 202 is flat when shipped or otherwise not attached to the body 102, but the inner diameter 203 is stretched when mounted on the body 102, in this way causing the ring to achieve a wavy or otherwise non-flat disposition. In other words, the stretching of the protective ring 202 may create a wavy geometry. Embodiments that exhibit rigidity may be more suitable for some of the mounting applications than others. In other embodiments, the protective ring 202 is made of a flexible material that allows the protective ring 202 to be mounted to the body 102 during shipment, and the protective ring 202 unfolds or returns to a flatter disposition when the applicator is removed from its packaging.

Also, the surface of the protective ring 202 may be smooth, rough, or have another finish. In some embodiments, the protective ring 202 is made of an absorbent material. In other embodiments, the protective ring 202 has at least two layers, and one of the layers is an absorbent material.

Additionally, the angle that the protective ring 202 extends away from the body 102 may be perpendicular to the surface of the body 202 or may be at an angle, either towards or away from the top of the applicator.

FIG. 11 depicts a top view of another embodiment of a protective ring 204. The illustrated embodiment includes a series of cuts or slits 205 around the inner diameter 203 in order to facilitate movement of the individual tab portions during mounting the protective ring 202 to the body 102 of the applicator. In other embodiments, a different arrangement of slits or other physical characteristics may be used. In the illustrated embodiment, the slits 205 are cuts or perforations extending radially outward from the inner diameter 203. The slits 205 are spaced equidistantly around the inner diameter 203 of the protective ring 204. The slits 205 may be present in all the different configurations described herein even if not specifically described. The slits 205 allow for the material to be more flexible at the inner diameter 203 and to allow for the protective ring 204 to more easily fit around the retention structure (described more fully in FIGS. 14-16).

FIG. 12 depicts a top view of another embodiment of a protective ring 206. The illustrated embodiment has an oval-shaped outer perimeter, instead of a circular outer perimeter. The illustrated embodiment also includes slits 205 on the inner diameter 203 of the protective ring 206. The illustrated embodiment includes eight slits 205 spaced equidistant around the inner diameter 203. Other embodiments may include fewer or more slits.

FIG. 13 depicts a top view of another embodiment of a protective ring 208. The illustrated embodiment has a rectilinear-shaped outer perimeter. Other embodiments may have different shapes for the outer perimeter of the protective ring. The illustrated embodiment also includes slits 205 on the inner diameter 203 of the protective ring 208. The illustrated embodiment includes eight slits 205 spaced equidistant around the inner diameter 203. Other embodiments may include fewer or more slits.

Figure 14:
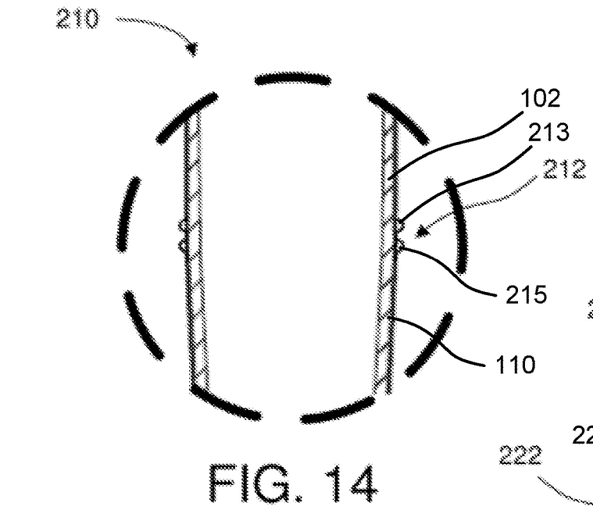
FIG. 14 depicts a detailed view of one embodiment of a ring retention structure on the body of a tampon applicator according to one or more embodiments of the present disclosure.

FIG. 14 depicts a detailed view 210 of one embodiment of a ring retention structure 212 on the body of a tampon applicator. The illustrated embodiment includes a pair of circular or arcuate protrusions from the body 102 in order to define a mounting channel for a protective ring. The raised protrusions may be continuous around the body of the applicator or, alternatively, may be discrete bumps disposed at different locations circumferentially around the body of the applicator. The portion of the body 102 below the retention structure 212 includes the pinch zone 110.

The retention structure 212 includes an upper protrusion 213 and a lower protrusion 215 with a gap between the upper protrusion 213 and the lower protrusion 215. The size of the gap and distance between the upper protrusion 213 and the lower protrusion 215 may correspond approximately to a thickness of the protective ring 202, 204, 206, 208 (see FIGS. 9-13 for examples). The protective ring 202 is configured to be seated in the gap between the upper protrusion 213 and the lower protrusion 215 such that the inner diameter of the protective ring 202 fits snugly or abuts the body 102 at the gap. The upper protrusion 213 acts as a mechanical interference to restrict movement of the protective ring 202 upwards once the protective ring 202 is seated. The lower protrusion 215 acts as a mechanical interference to restrict movement of the protective ring 202 downwards once the protective ring 202 is seated.

In some embodiments, the upper protrusion 213 and the lower protrusion 215 are approximately the same size and shape allowing for a user to slide the protective ring 202 into position from above or below. That is, the protective ring 202 may be slid into position over the upper protrusion 213 from above or the protective ring 202 may be slid into position over the lower protrusion 215 from below.

In some embodiments, the upper protrusion 213 may be larger than the lower protrusion 215. In such embodiments, the protective ring 202 would only be slid into position from below. Other embodiments may have an opposite configuration with the lower protrusion 215 being larger than the upper protrusion 213. In such embodiments, the protective ring 202 would only be slid into position from above.

Figure 15:
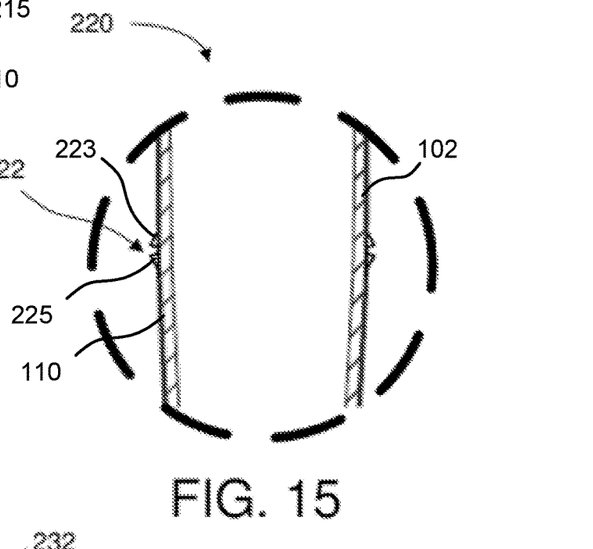
FIG. 15 depicts a detailed view of another embodiment of a ring retention structure on the body of a tampon applicator according to one or more embodiments of the present disclosure.

FIG. 15 depicts a detailed view 220 of another embodiment of a ring retention structure 222 on the body of a tampon applicator. The illustrated embodiment includes angular protrusions, instead of the rounded protrusions of FIG. 14, in order to define a mounting channel for the protective ring 202. The raised protrusions may be continuous around the body of the applicator or, alternatively, may be discrete bumps disposed at different locations circumferentially around the body of the applicator. The portion of the body 102 below the retention structure 222 includes the pinch zone 110.

The retention structure 222 includes an upper angled protrusion 223 and a lower angled protrusion 225 with a gap between the upper angled protrusion 223 and the lower protrusion 225. The size of the gap and distance between the upper angled protrusion 223 and the lower angled protrusion 225 may correspond approximately to a thickness of the protective ring 202, 204, 206, 208 (see FIGS. 9-13 for examples). The protective ring 202 is configured to be seated in the gap between the upper angled protrusion 223 and the lower protrusion 225 such that the inner diameter of the protective ring 202 fits snugly or abuts the body 102 at the gap.

The upper angled protrusion 223 acts as a mechanical interference to restrict movement of the protective ring 202 upwards once the protective ring 202 is seated. As shown, the surface angle of the upper angled protrusion 223 is more pronounced on the bottom portion as compared to the upper portion. This allows for the protective ring 202 to more easily move over the upper angle protrusion 223 in the direction into a seated position. Once seated, the more severe surface angle restricts movement of the protective ring 202 out of a seated position.

The lower angled protrusion 225 also acts as a mechanical interference to restrict movement of the protective ring 202 downwards once the protective ring 202 is seated. The surface angles of the lower angled protrusion 225 are opposite to the upper angled protrusion 223 allowing for the protective ring 202 to more easily move upwards than downwards (opposite of the upper angled protrusion 223).

In some embodiments, the upper protrusion 213 and the lower protrusion 215 are approximately the same size and shape allowing for a user to slide the protective ring 202 into position from above or below. That is, the protective ring 202 may be slid into position over the upper protrusion 213 from above or the protective ring 202 may be slid into position over the lower protrusion 215 from below.

In some embodiments, the upper protrusion 213 may be larger than the lower protrusion 215. In such embodiments, the protective ring 202 would only be slid into position from below. Other embodiments may have an opposite configuration with the lower protrusion 215 being larger than the upper protrusion 213. In such embodiments, the protective ring 202 would only be slid into position from above.

Figure 16:
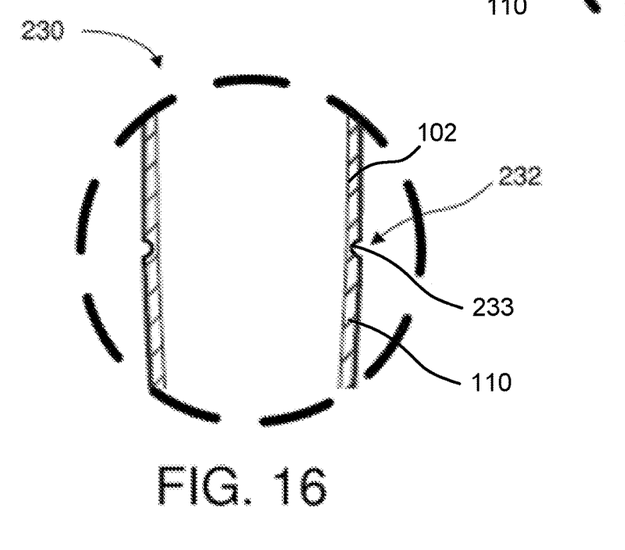
FIG. 16 depicts a detailed view of another embodiment of a ring retention structure on the body of a tampon applicator according to one or more embodiments of the present disclosure.

FIG. 16 depicts a detailed view 230 of another embodiment of a ring retention structure 232 on the body of a tampon applicator. The illustrated embodiment includes a circular depression or depressed channel 233 that forms a ring circumferentially around the body 102 of the applicator so a protective ring 202 can mount into the channel formed by the depressed channel 233. Other embodiments may use other forms of retainers or retention structures for the protective rings.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the foregoing disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A tampon applicator system comprising:
    a tampon applicator comprising a body, a stem configured to slide into the body, and a protective ring extending outward from the body;
    wherein the body comprises:
        a pinch zone;
        an opening, wherein the pinch zone is at an opposite end of the body from the opening; and
        an internal structure disposed at the opposite end of the body from the opening and abuts an end of the pinch zone, the internal structure protrudes out of an interior surface of the body,
    wherein the stem comprises a proximal end and proximal locking beads on its outer surface, the stem being configured to interact with the internal structure to retain the proximal end of the stem inside the body and the proximal locking beads outside of the body,
    wherein the proximal locking beads are configured to be forced past the internal structure into the body when a user applies a force to the stem to push a tampon out of the tampon applicator,
    wherein the pinch zone is disposed on the body below the protective ring,
    wherein the protective ring is configured to protect the pinch zone from exposure on the opposite side of the protective ring.

2. The tampon applicator system of claim 1, wherein the stem further comprises distal locking beads at a distal end of the stem.

3. The tampon applicator system of claim 2, wherein the stem is configured to slide completely within the body.

4. The tampon applicator system of claim 3, wherein the proximal locking beads are molded into the proximal end of the stem and the distal locking beads are molded into the distal end of the stem.

5. The tampon applicator system of claim 1, wherein the protective ring is molded into the body, such that the body and protective ring form a unitary piece.

6. The tampon applicator system of claim 1, wherein the protective ring is a separate piece from the body and the protective ring is mounted to the body.

7. The tampon applicator system of claim 6, wherein the body further comprises a retention structure on an exterior surface of the body.

8. The tampon applicator system of claim 7, wherein the retention structure comprises an upper protrusion and a lower protrusion.

9. The tampon applicator system of claim 8, wherein the protective ring is configured to couple to the body and be seated between the upper protrusion and the lower protrusion.

10. The tampon applicator system of claim 9, wherein the upper protrusion and the lower protrusion are angled protrusions.

11. The tampon applicator system of claim 7, wherein the retention structure comprises a depressed channel circumferentially around the body.

12. The tampon applicator system of claim 11, wherein the protective ring is configured to couple to the body and be seated in the depressed channel.

13. The tampon applicator system of claim 6, wherein the protective ring further comprises a series of slits on an inner diameter of the protective ring, the slits extending radially outward, wherein the series of slits are configured to facilitate flexing of the inner diameter while mounting the protective ring to the body.

14. The tampon applicator system of claim 1, wherein the protective ring is sloped downward towards the pinch zone and away from the opening.

15. The tampon applicator system of claim 1, wherein the protective ring further comprises a series of slits on an inner diameter of the protective ring, the slits extending radially outward, wherein the series of slits are configured to facilitate flexing of the inner diameter while mounting the protective ring to the body.

* * * * *